United States Patent [19]

Goebel et al.

[11] 4,183,367

[45] Jan. 15, 1980

[54] ENHANCING THE DRYING OF HAIR BY THE USE OF FLUORINATED CATONIC AND AMPHOTERIC SURFACTANTS

[75] Inventors: James C. Goebel, Stamford, Conn.; Anthony C. Lunn, Pleasantville, N.Y.

[73] Assignee: American Cyanamid Company, Stamford, Conn.

[21] Appl. No.: 853,712

[22] Filed: Nov. 21, 1977

Related U.S. Application Data

[63] Continuation-in-part of Ser. No. 693,582, Jun. 17, 1976, abandoned.

[51] Int. Cl.$^2$ ............................................. A45D 19/16
[52] U.S. Cl. ................................. 132/7; 252/DIG. 13; 252/DIG. 14; 252/544; 252/545; 252/546; 252/547; 424/70
[58] Field of Search ............... 252/DIG. 13, DIG. 14, 252/544, 545, 546, 547; 424/70; 8/94, 188, 189; 132/7

[56] References Cited

U.S. PATENT DOCUMENTS

| | | | |
|---|---|---|---|
| 3,147,065 | 9/1964 | Koshar et al. | 8/188 |
| 3,147,066 | 9/1964 | Brown et al. | 8/188 |
| 3,510,494 | 5/1970 | Gagliardi | 8/188 X |
| 3,585,145 | 6/1971 | Fethke | 252/526 X |
| 3,622,590 | 11/1971 | Gresham | 8/188 X |
| 3,959,462 | 5/1976 | Parks et al. | 424/70 |
| 3,972,998 | 8/1976 | Keiner | 424/70 |
| 3,993,744 | 11/1976 | Cella et al. | 424/70 |
| 3,993,745 | 11/1976 | Cella et al. | 424/70 X |
| 4,013,786 | 3/1977 | Cella et al. | 424/70 |
| 4,066,746 | 1/1978 | Callingham | 424/70 X |

*Primary Examiner*—James O. Thomas, Jr.
*Assistant Examiner*—Vera C. Clarke
*Attorney, Agent, or Firm*—Charles J. Fickey

[57] ABSTRACT

The use of fluorinated cationic and amphoteric surfactants in shampoos in order to promote more rapid drying of washed hair is disclosed.

4 Claims, No Drawings

ENHANCING THE DRYING OF HAIR BY THE USE OF FLUORINATED CATONIC AND AMPHOTERIC SURFACTANTS

This is a continuation-in-part of our previous application Ser. No. 693,582, filed June 17, 1976, now abandoned.

This invention relates to a method for treating hair so that it dries more quickly after being washed. More specifically, this invention relates to shampoo compositions and to rinse compositions, for example, creme rinses, which leave the hair with less trapped moisture and therefore allow the hair to dry faster after washing.

Drying hair subsequent to washing is a time consuming operation, both in commercial beauty establishments and in home applications. Therefore, any product which offers the advantages of allowing the hair to dry faster subsequent to washing will afford valuable savings of time for the home user, as well as valuable savings of time and money for commercial applications.

When washed, or otherwise treated with water, hair both absorbs water into the fiber and traps, by capillary action, water in the spaces between fibers. The water absorbed by the hair fiber may vary from about 30% of the dry fiber weight for virgin hair to as much as 60% of dry fiber weight for heavily damaged hair, and the water held in capillary spaces between the hairs may be in excess of 130% of the dry fiber weight. Towel drying of the hair does not remove water absorbed in the fiber, and leaves between about 10 and 50% water, based on the dry weight of the hair, remaining in the capillary spaces between the hairs. The compositions of the present invention aid the drying of hair by reducing the amount of water retained in the capillaries between the hair rather than by decreasing the amount of moisture absorbed by the hair.

Recent patents (Keiner, Canadian Pat. No. 935,379 and Callingham et al., British Pat. No. 1,268,636) have disclosed that fluorine containing polymers may be used in hair treating compositions in order to promote faster drying of wet hair. The polymers used in these references were either copolymers of vinyl monomers and the following fluorine containing monomer:

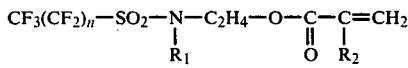

wherein $R_1$ is an alkyl group containing 1 to 6 carbon atoms, $R_2$ is hydrogen or methyl; and n is an integer from 3 to 11, or copolymers (with vinyl monomers) or homopolymers of the following fluorine containing monomer:

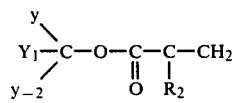

wherein $R_2$ is as defined above, y, $y_1$, $y_2$, are partially or totally fluorinated alkyl groups containing from 1 to 11 carbon atoms and are not necessarily the same. In other words, the polymers disclosed consist of a polymeric carbon chain backbone having fluorine containing substituents attached thereto. The polymers are not soluble in water, and when used in aqueous based compositions are applied in the form of an emulsion.

Cassidy (U.S. Pat. No. 3,814,110) has recently disclosed that the drying time of hair may be improved by rinsing the hair subsequent to washing with a rinse water containing any organic surfactant which is able to reduce the surface tension of water to a value between 5 and 70% below the normal surface tension of water. According to Cassidy, the reduction of the surface tension of the rinse water is the critical factor, rather than the wetting agent used in the rinse water; although, nonionic wetting agents are preferred. However, tests of water pick-up of lightly blotted hair rinsed with water whose surface tension had been reduced to between 8.3% and 73.6% below the normal value through the addition of nonionic surfactants, did not show any reduction in the water pick-up of the hair.

It is an object of the present invention to provide shampoo, creme rinse, and rinse water compositions which decrease the amount of water picked up by hair treated with the compositions, and thereby decrease the drying time of treated hair.

According to the present invention, it has been discovered that certain cationic and amphoteric fluorochemical surfactants having the formula shown in Formula I may be added to shampoos, creme rinses, and rinse water, in order to reduce the amount of water retained in the hair and thereby promote faster drying of the hair.

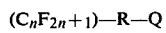

wherein n is an integer from 4 to 18, R is selected from the group consisting of —X—,—Y—O—Z—, —Y—S—Z—,

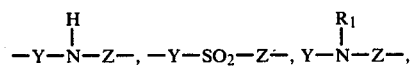

—Y—CONH—Z— Y—SO$_2$NH—Z—, wherein X is $(CH_2)_x$, Y is $(CH_2)_y$, and Z is $(CH_2)_z$, $R_1$ is an alkyl group containing from 1 to 4 carbon atoms, wherein X is an integer from 1 to 6, the terminal $(CH_2)_y$ group is attached to the $(C_nF_{2n+1})$ portion of the molecule, the terminal $(CH_2)_z$ group is attached to the Q portion of the molecule, y is an integer from 0 to 3, z is an integer from 1 to 3, and Q is selected from the group consisting of

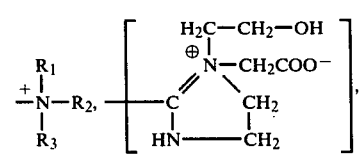

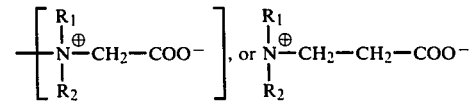

wherein $R_1$, $R_2$ and $R_3$ are alkyl groups containing from 1 to 4 carbon atoms.

Commercially available surfactants which fall within the definition of Formula I are Zonyl FSB, an amphoteric fluorochemical surfactant manufactured by E. I. DuPont de Nemours & Company; Zonyl FSC, a cationic fluorochemical surfactant manufactured by E. I. duPont de Nemours & Company; and FC-134, a cationic fluorochemical surfactant manufactured by Minnesota Mining & Manufacturing.

It is important to note that the effect of fluorochemical surfactants in improving the drying time of wet hair is limited to those surfactants which are amphoteric or cationic. Nonionic or anionic surfactants are ineffective even if they contain fluorine. This limitation does not obtain, however, in the case of fluorine containing polymers, for the polymers which are the subjects of Canadian Pat. No. 935,379 and British Pat. No. 1,268,636, noted above, exert an effect on the drying of hair even though the molecules do not have centers of charge.

The effect of the amphoteric and cationic surfactants of the present invention is greatest when dry hair or wet hair is rinsed with a solution of the appropriate surfactants. The water retention of the hair is also appreciably reduced when the surfactants are added to shampoo or creme rinse formulations. The amphoteric surfactants are compatible with nonionic, cationic and anionic surfactants, and thus may be used in all types of shampoo and creme rinse combinations. The cationic surfactants are generally limited to use in compositions containing nonionic or cationic surfactants However, in compositions of high detergency, the fluorochemical surfactants of Formula I are somewhat less effective than they would be in composition of lesser detergency. For example, a shampoo containing an amphoteric surfactant shown in Formula I in addition to relatively large amounts of highly detergent surfactants, such as alkyl sulfate surfactants, would be less effective in promoting the rapid drying of hair subsequent to shampooing than a shampoo composition of lesser detergency containing the same quantity of such an amphoteric surfactant.

As noted above, the surfactants of Formula I may be used in rinse water subsequent to shampooing. In rinse compositions containing such surfactants, the surfactant is effective in concentrations below 0.05%, but may be used in concentrations in excess of 1% of the rinse water. It is interesting to note, however, that there is no significant enhancement of the effect on the drying time in going from 0.05% surfactant rinse solution to 1% surfactant in the rinse solution. Thus, the greatest economy may be achieved by using the surfactants of Formula I at the lowest possible concentration.

Since the surfactants of Formula I are soluble in lower alcohols such as methyl, ethyl, n-propyl and isopropyl alcohols, it is possible to add lower alcohols to the rinse compositions described above. Hair rinsed in aqueous solutions of lower alcohols is known to dry faster than hair rinsed in pure water, and the addition of a surfactant of Formula I to an aqueous lower alcohol solution creates a rinse solution which promotes faster drying of hair than is possible with a pure water, aqueous lower alcohol solutions, or aqueous solution of the surfactants themselves. Such rinses may be prepared in useable form or in a form requiring dilution by the user. Whatever the actual concentration of lower alcohol in the preparation, however, the solution which remains on the hair, optimally contains about 10–30% alcohol. Lower concentrations of alcohol do not significantly lower the drying time, while higher concentrations, although effective, present a fire hazard, especially if the consumer uses an electric hair dryer subsequent to the use of the rinse.

In addition, it is possible to add small amounts of cationic conditioners to the alcohol containing fluorosurfactant rinses discussed above. Such compositions are used as a final rinse in the same manner as the rinses disclosed above. However, rinses containing conditioners provide a creme rinse action in addition to faster drying of the hair.

The term cationic conditioner is used to denote those quaternary ammonium compounds commonly used in creme rinses, such as lauryl trimethyl ammonium chloride, dialkyl dimethyl ammonium bromide, stearyl dimethyl benzyl ammonium chloride, and described more generally by Formula II.

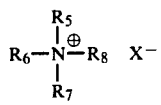

wherein $R_5$ and $R_6$ are both methyl groups, $R_7$ is methyl or $C_{10}$–$C_{18}$ alkyl, $R_8$ is $C_{10}$–$C_{18}$ alkyl or benzyl, and X is chloride or bromide. The term cationic conditioner is also used herein to describe the cationic surfactants which are compatible with anionics, as disclosed in Cosmetics and Perfumery, Volume 10, Pages 74 and 75, March, 1975.

In shampoo compositions as little as 0.1% of the amphoteric surfactants of Formula I have been found to be effective in reducing the amount of water retained by the hair washed with the shampoo, although amounts as large as 5% may be used without difficulty. While such surfactants may be used in any shampoo composition to reduce the amount of water retained by hair which is washed with the shampoo, as noted above, it is more effective in shampoo compositions of lower detergency. Thus, it is desirable when formulating shampoos containing such amphoteric surfactants to avoid such strong detergent ingredients as alkyl benzene sulfonates. However, compositions containing such amphoteric surfactants in conjunction with moderate quantities of alkyl sulfates are effective in lowering the amount of water retained by the hair subsequent to shampooing. Since the amphoteric surfactants are compatible with nonionic, cationic, and anionic surfactants, they may be used in all types of shampoo formulations, including those with a high pH, those with a lower pH, as well as shampoo formulation containing nonionic surfactants or cationic conditioners. In other words, the great compatibility of the amphoteric fluorosurfactants of Formula I with all types of surfactants allows their use in any shampoo composition. The following references provide some examples of shampoo formulations in which the amphoteric surfactants may be used: Sagarin, *Cosmetic Science and Technology*, pages 380–421, Interscience Publishers (1957); and Shampoo Formulation, in *Cosmetics and Perfumery*, Volume 90, pages 105–118, March 1975.

In creme rinse compositions 1% of the amphoteric or cationic surfactants of Formula I have been found effective in lessening the amount of water which remains on the hair subsequent to rinsing. These surfactants are compatible with cationic surfactants generally, and in particular with the cationic conditioner noted above, and thus will be effective in any creme rinse based on cationic conditioners. Since the surfactants of Formula I are compatible with nonionic materials, they will also be effective in those creme rinse compositions which are based on nonionic conditioners.

The following examples are provided for illustrative purposes and may include particular features of the invention. However, the examples should not be construed to limit the invention, many variations of which are possible without departing from the spirit or scope thereof.

EXAMPLE 1

A Water Rinse Containing Zonyl FSB, Zonyl FSC or FC-134

A solution containing 0.05% Zonyl FSB, or Zonyl FSC, or FC-134, or mixtures of these three surfactants in a total surfactant concentration of 0.05% is prepared. When hair is rinsed with this solution subsequent to shampooing, there is a decrease in the drying time of the hair.

EXAMPLE 2

A Water Rinse Concentrate Containing Alcohol and Zonyl FSB, Zonyl FSC or FC-134

| Ethyl Alcohol | 50% |
|---|---|
| Zonyl FSB | 0.2% |
| Water to | 100% |

This concentrate may be used either by applying a small quantity to the wet hair in such a manner that the liquid remaining on the hair contains between 10–30% alcohol. Alternatively, the concentrate may be diluted with water to form a final rinse containing between 10 and 30% alcohol. A larger volume of the dilute final rinse may then be used to rinse the wet hair. Similar compositions may be prepared substituting Zonyl FSC or FC-134 for all or part of the Zonyl FSB. When hair is rinsed with this solution subsequent to shampooing, there is a decrease in the drying time of the hair.

EXAMPLE 3

A Water Rinse Concentrate Containing Zonyl FSB, Zonyl FSC, or FC-134 and a cationic conditioner

| Ethyl Alcohol | 50% |
|---|---|
| Zonyl FSB | 0.2% |
| Stearyl Dimethyl Benzyl Ammonium Chloride | 0.2% |
| Water to | 100% |

The rinse concentrate may be used in the same manner as the rinse concentrate of Example 2. Similar compositions may be prepared substituting Zonyl FSC or FC-134 for all or part of the Zonyl FSB. In addition to providing faster drying time, the compositions have a creme rinse effect on the hair.

EXAMPLE 4

An Anionic Shampoo Containing Zonyl FSB

| Sodium Lauryl Sulfate | 3.0% |
|---|---|
| Triethanolamine Lauryl Sulfate | 4.0% |
| Triethanolamine | 5.0% |
| Lauramide Diethanolamine | 4.0% |
| Zonyl FSB | 1.0% |
| Water to | 100.0% |

Hair washed with this shampoo dries more quickly than hair washed in similar compositions without Zonyl FSB. All, or part, of the Zonyl FSB may be replaced by FC-134.

EXAMPLE 5

A Creme Rinse With Cationic Conditioners

| Distearyl Dimethyl Ammonium Chloride | 2.0% |
|---|---|
| Stearyl Dimethyl Benzyl Ammonium Chloride | 1.0% |
| Glycerol Monostearate | 2.0% |
| Zonyl FSB | 1.0% |
| Water to | 100.0% |

Hair rinsed with this creme rinse dries more quickly than hair rinsed with similar creme rinse compositions which do not contain the surfactants of Formula I.

EXAMPLE 6

A Creme Rinse With Cationic Conditioners

| Distearyl Dimethyl Ammonium Chloride | 2.0% |
|---|---|
| Stearyl Dimethyl Benzyl Ammonium Chloride | 1.0% |
| Glycerol Monostearate | 2.0% |
| Zonyl FSC | 1.0% |
| Water to | 100.0% |

Hair rinsed with this creme rinse dries more quickly than hair rinsed with similar creme rinse compositions which do not contain the surfactants of Formula I.

Formulations of this invention were compared to the prior art and the results are shown in Table I.

Table I

Water Pick-up of Rinsed, Lightly Blotted, Virgin Hair at Reduced Surface Tensions

| Aqueous Solution | Surface Tension dynes/cm | % below pure water | Water pick-up of hair as a percentage of dry weight |
|---|---|---|---|
| Water | 72 | 0 | 71 |
| Triton x-100, 0.0001% | 66 | 8.3 | 72 |
| Triton x-100, 0.0005% | 53 | 26.4 | 69 |
| Triton x-100, 0.001% | 46 | 36.1 | 66 |
| Triton x-100, 0.005% | 36 | 50 | 69 |
| Triton x-100, 0.01% | 31 | 56.9 | 67 |
| FC-170[2], 0.1% | 19 | 73.6 | 70 |
| Zonyl FSB[3] 0.1% | 17 | 76.4 | 61 |
| Zonyl FSB, 1.0% | 17 | 76.4 | 55 |
| Zonyl FSC[4] 1.0% | | | 55 |
| FC-134[5] 1.0% | 15 | 79.2 | 55 |

[1]Triton x-100: a nonionic octylphenoxy polyethoxy ethanol surfactant manufactured by Rohm & Haas.
[2]FC-170: a nonionic fluorochemical surfactant manufactured by Minnesota Mining & Manufacturing.
[3]Zonyl FSB: an amphoteric fluorochemical surfactant manufactured by E. I. duPont de Nemours & Company.
[4]Zonyl FSC: a cationic fluorochemical surfactant manufactured by E. I. duPont de Nemours & Company.
[5]FC-134: a cationic fluorochemical surfactant manufactured by Minnesota Mining & Manufacturing.

We claim:

1. A method for enhancing the drying of hair when water or an aqueous composition is applied, comprising applying thereto an aqueous solution containing from about 0.05 to 5% of a cationic or amphoteric compound having the formula:

$$(C_nF_{2n+1})-R-Q$$

wherein n is an integer from 4 to 18, R is selected from the group consisting of $(CH_2)_x$, $(CH_2)_y-O-(CH_2)_z$, $(CH_2)_y-S-(CH_2)_z$,

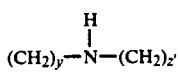

wherein x is an integer from 1 to 6, the terminal $(CH_2)_y$ group is attached to the $(C_nF_{2+1})$ portion of the molecule, the terminal $(CH_2)_z$ group is attached to the Q portion of the molecule, y is an integer from 0 to 3, z is an integer from 1 to 3 and Q is selected from the group consisting of:

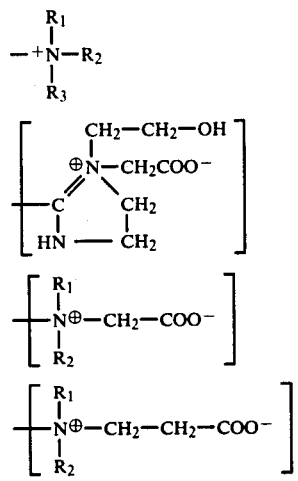

2. The method according to claim 1 wherein the aqueous solution also contains shampoo detergents.

3. The method according to claim 1 wherein the treatment of said hair is followed by a water rinse.

4. A method of treating hair to enhance drying which comprises the steps of applying thereto a composition consisting essentially of an aqueous solution of from about 10 to 30% of a lower alcohol selected from the group consisting of methanol, ethanol n-propanol and isopropanol, from about 0.05 to 1% of a cationic or amphoteric compound of the formula:

wherein n is an integer from 4 to 18, R is selected from the group consisting of $(CH_2)_x$, $(CH_2)_y-O-(CH_2)_z$, $(CH_2)_y-S-(CH_2)$,

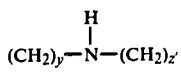

wherein x is an integer from 1 to 6, the terminal $(CH_2)_z$ group is attached to the $(C_nF_{2n+1})$ portion of the molecule, the terminal $(CH_2)_z$ group is attached to the Q portion of the molecule, y is an integer from 0 to 3, z is an integer from 1 to 3, and Q is selected from the group consisting of:

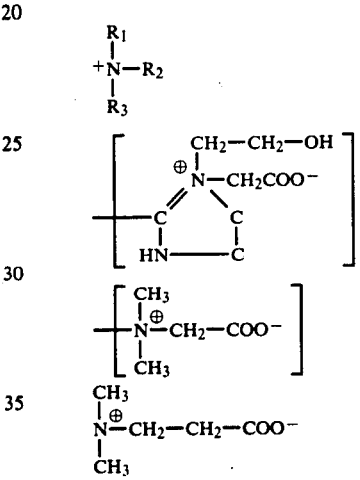

wherein $R_1$, $R_2$, and $R_3$ are alkyl groups containing from 1 to 4 carbon atoms, and 0–5% of a cationic conditioner, and therefafter rinsing said aqueous solution from the hair with water.

* * * * *